(12) United States Patent
Monty

(10) Patent No.: US 11,793,663 B2
(45) Date of Patent: Oct. 24, 2023

(54) DRESSING FOR CONCEALING A STRUCTURE ON A HUMAN BODY

(71) Applicant: Ostique Limited, London (GB)

(72) Inventor: Stephanie Monty, London (GB)

(73) Assignee: Ostique Limited, London (GB)

(*) Notice: Subject to any disclaimer, the term of this patent is extended or adjusted under 35 U.S.C. 154(b) by 827 days.

(21) Appl. No.: 16/211,254

(22) Filed: Dec. 6, 2018

(65) Prior Publication Data
US 2019/0175386 A1   Jun. 13, 2019

Related U.S. Application Data

(63) Continuation of application No. PCT/GB2017/051652, filed on Jun. 7, 2017.

(30) Foreign Application Priority Data

Jun. 7, 2016 (GB) .................................... 1609954

(51) Int. Cl.
| A61F 5/445 | (2006.01) |
| A61F 13/00 | (2006.01) |
| A61F 13/02 | (2006.01) |
| A61B 5/00 | (2006.01) |

(52) U.S. Cl.
CPC ........ *A61F 5/445* (2013.01); *A61F 13/00059* (2013.01); *A61F 13/0266* (2013.01); *A61B 5/6833* (2013.01); *A61F 13/00063* (2013.01)

(58) Field of Classification Search
CPC .. A61B 5/6833; A61F 5/445; A61F 13/00059; A61F 13/0266; A61F 13/00063
See application file for complete search history.

(56) References Cited

U.S. PATENT DOCUMENTS

| 2,327,514 | A | * | 8/1943 | Fenwick | ................. A61F 5/445 604/338 |
| 2,542,233 | A | * | 2/1951 | Carroll | .................... A61F 5/445 604/337 |
| 2,544,579 | A | * | 3/1951 | Ardner | .................... A61F 5/445 604/337 |
| 4,211,224 | A | * | 7/1980 | Kubach | ................... A61F 5/441 604/333 |

(Continued)

FOREIGN PATENT DOCUMENTS

| FR | 2425240 | 12/1979 |
| WO | WO 99/36017 | 7/1999 |

(Continued)

OTHER PUBLICATIONS

International Search Report and the Written Opinion dated Nov. 6, 2017 From the International Searching Authority Re. Application No. PCT/GB2017/051652. (14 Pages).

(Continued)

*Primary Examiner* — Guy K Townsend

(57) ABSTRACT

The present invention relates to surgical, medical or other anatomical dressings that may be applied to the human body. In particular, the invention relates to a dressing for concealing a structure (in particular, a stoma) on a human body, the dressing comprising a patch arranged to be placed on the body; wherein the patch has an indentation for receiving the structure so as to conceal the structure when the patch is placed on the body.

12 Claims, 14 Drawing Sheets

(56) References Cited

U.S. PATENT DOCUMENTS

| | | | | |
|---|---|---|---|---|
| 5,423,782 | A * | 6/1995 | Wolrich | A61F 5/445 604/339 |
| 5,672,163 | A * | 9/1997 | Ferreira | A61F 5/441 604/333 |
| 6,135,986 | A * | 10/2000 | Leisner | A61F 5/441 604/324 |
| 6,689,111 | B2 * | 2/2004 | Mulhauser | A61F 5/445 604/332 |
| 6,709,421 | B1 * | 3/2004 | Falconer | A61F 5/445 604/335 |
| 7,087,041 | B2 * | 8/2006 | von Dyck | A61F 5/445 604/338 |
| 7,166,091 | B1 * | 1/2007 | Zeltner | A61F 5/445 604/338 |
| 7,326,190 | B2 * | 2/2008 | Botten | A61F 5/441 604/332 |
| 7,341,578 | B2 * | 3/2008 | Bulow | A61F 5/441 604/338 |
| 7,347,844 | B2 * | 3/2008 | Cline | A61F 5/448 604/338 |
| 7,367,965 | B2 * | 5/2008 | Poulsen | A61F 5/441 604/324 |
| 7,559,922 | B2 * | 7/2009 | Botten | A61F 5/441 604/332 |
| 7,625,362 | B2 * | 12/2009 | Boehringer | A61M 1/74 604/304 |
| 7,765,006 | B2 * | 7/2010 | Martino | A61N 1/36007 607/40 |
| 7,765,007 | B2 * | 7/2010 | Martino | A61N 1/36007 607/40 |
| 7,857,796 | B2 * | 12/2010 | Cline | A61F 5/448 604/277 |
| 7,981,098 | B2 * | 7/2011 | Boehringer | A61M 1/74 604/319 |
| 8,070,737 | B2 * | 12/2011 | Cline | A61F 5/445 604/277 |
| 8,092,437 | B2 * | 1/2012 | Cline | A61F 5/445 604/277 |
| 8,217,221 | B2 * | 7/2012 | Davies | A61F 5/445 604/378 |
| 8,221,368 | B2 * | 7/2012 | Forbes | A61F 5/445 600/32 |
| 8,377,020 | B1 * | 2/2013 | Berven | A61F 5/445 604/335 |
| 8,684,982 | B2 * | 4/2014 | Nguyen-DeMary | A61F 5/441 604/327 |
| 8,845,606 | B2 * | 9/2014 | Nguyen-Demary | A61F 5/445 604/338 |
| 8,939,952 | B2 * | 1/2015 | Weig | A61F 5/451 604/355 |
| 8,979,811 | B2 * | 3/2015 | Keleny | B01D 46/02 604/338 |
| 9,078,764 | B2 * | 7/2015 | Davies | A61F 5/445 |
| 9,345,612 | B2 * | 5/2016 | Hanuka | A61F 5/448 |
| 9,517,157 | B2 * | 12/2016 | Hanuka | A61F 5/4407 |
| 9,549,839 | B2 * | 1/2017 | Schertiger | A61F 5/441 |
| 9,636,249 | B2 * | 5/2017 | Davies | A61F 5/445 |
| 9,707,120 | B2 * | 7/2017 | Nguyen-DeMary | A61F 5/441 |
| 9,833,352 | B2 * | 12/2017 | Maidl | A61F 5/445 |
| 9,883,964 | B2 * | 2/2018 | Hanuka | A61F 5/4404 |
| 10,251,773 | B2 * | 4/2019 | Schertiger | A61F 5/4405 |
| 10,524,953 | B2 * | 1/2020 | Hanuka | A61F 5/4404 |
| 10,646,370 | B2 * | 5/2020 | Keleny | A61F 5/441 |
| 10,653,551 | B2 * | 5/2020 | Apolinario | A61F 5/441 |
| 11,039,950 | B2 * | 6/2021 | Jones, Jr. | A61F 5/442 |
| 11,076,978 | B2 * | 8/2021 | Nguyen-Demary | A61F 5/445 |
| 11,291,579 | B2 * | 4/2022 | Hanuka | A61F 5/4407 |
| 2002/0077611 | A1 * | 6/2002 | von Dyck | A61F 5/442 604/332 |
| 2003/0181879 | A1 * | 9/2003 | Mulhauser | A61F 5/445 604/332 |
| 2003/0187393 | A1 * | 10/2003 | Cline | A61F 5/445 604/131 |
| 2004/0181197 | A1 * | 9/2004 | Cline | A61F 5/445 604/337 |
| 2004/0193122 | A1 * | 9/2004 | Cline | A61F 5/448 604/332 |
| 2005/0070863 | A1 * | 3/2005 | Bulow | A61F 5/441 604/332 |
| 2005/0085779 | A1 * | 4/2005 | Poulsen | A61F 5/441 604/332 |
| 2005/0261645 | A1 * | 11/2005 | Conrad | A61F 5/445 604/332 |
| 2006/0025727 | A1 * | 2/2006 | Boehringer | A61M 1/966 604/313 |
| 2006/0058577 | A1 * | 3/2006 | Davies | A61F 5/441 600/32 |
| 2006/0206069 | A1 * | 9/2006 | Cline | A61F 5/445 604/332 |
| 2006/0271002 | A1 * | 11/2006 | Botten | A61F 5/441 604/339 |
| 2007/0123832 | A1 * | 5/2007 | Cline | A61F 5/445 604/335 |
| 2007/0191794 | A1 * | 8/2007 | Cline | A61F 5/445 604/335 |
| 2008/0033378 | A1 * | 2/2008 | Worsoee | A61F 5/441 604/333 |
| 2008/0091154 | A1 * | 4/2008 | Botten | A61F 5/441 96/155 |
| 2009/0012501 | A1 * | 1/2009 | Boehringer | A61M 1/966 604/543 |
| 2009/0157140 | A1 * | 6/2009 | Martino | A61N 1/36007 604/332 |
| 2009/0247970 | A1 * | 10/2009 | Keleny | B01D 46/0036 156/247 |
| 2009/0254054 | A1 * | 10/2009 | Blott | A61F 13/00063 604/290 |
| 2009/0275795 | A1 * | 11/2009 | Martino | A61F 5/445 600/32 |
| 2010/0010460 | A1 * | 1/2010 | Butler | A61F 5/441 604/333 |
| 2010/0022976 | A1 * | 1/2010 | Weig | A61F 5/451 604/355 |
| 2010/0069859 | A1 * | 3/2010 | Weig | A61F 2/0027 604/335 |
| 2010/0121291 | A1 * | 5/2010 | Davies | A61F 5/441 604/333 |
| 2010/0241092 | A1 * | 9/2010 | Nguyen-DeMary | A61F 5/4407 604/336 |
| 2012/0010580 | A1 * | 1/2012 | Forbes | A61F 5/441 604/338 |
| 2012/0179124 | A1 * | 7/2012 | Nguyen-Demary | A61F 5/448 604/335 |
| 2012/0220965 | A1 | 8/2012 | Ramjit et al. | |
| 2012/0283678 | A1 * | 11/2012 | Nguyen-DeMary | A61F 5/445 604/338 |
| 2013/0019374 | A1 * | 1/2013 | Schwartz | A61F 5/453 428/492 |
| 2013/0072886 | A1 * | 3/2013 | Schertiger | A61F 5/445 604/335 |
| 2013/0192604 | A1 * | 8/2013 | Persson | A61M 16/047 128/207.16 |
| 2013/0304008 | A1 * | 11/2013 | Hanuka | A61F 5/445 604/338 |
| 2014/0276501 | A1 * | 9/2014 | Cisko | A61F 5/443 604/355 |
| 2014/0364823 | A1 * | 12/2014 | Nguyen-Demary | A61F 5/448 604/335 |
| 2015/0141944 | A1 * | 5/2015 | Hanuka | A61F 5/442 604/338 |
| 2015/0257925 | A1 * | 9/2015 | Schwartz | A61F 13/2005 128/831 |
| 2015/0305916 | A1 * | 10/2015 | Hanuka | A61F 5/441 604/335 |
| 2016/0113810 | A1 * | 4/2016 | Hanuka | A61F 5/445 604/335 |

(56) References Cited

U.S. PATENT DOCUMENTS

| | | | | |
|---|---|---|---|---|
| 2016/0166424 | A1* | 6/2016 | Hanuka | A61F 5/445 |
| | | | | 604/335 |
| 2016/0235581 | A1* | 8/2016 | Keleny | A61F 5/441 |
| 2017/0143533 | A1* | 5/2017 | Schertiger | A61F 5/445 |
| 2017/0209294 | A1* | 7/2017 | Apolinario | A61F 5/441 |
| 2017/0281397 | A1* | 10/2017 | Davies | A61F 5/445 |
| 2017/0312115 | A1* | 11/2017 | Nguyen-DeMary | A61P 31/00 |
| 2018/0235802 | A1* | 8/2018 | Nguyen-Demary | A61F 5/445 |
| 2018/0333290 | A1* | 11/2018 | Jones | A61F 5/441 |
| 2019/0142627 | A1* | 5/2019 | Schwartz | A61F 13/2005 |
| | | | | 128/846 |
| 2019/0175386 | A1* | 6/2019 | Monty | A61F 5/445 |
| 2019/0290472 | A1* | 9/2019 | Schertiger | A61F 5/4405 |
| 2020/0237549 | A1* | 7/2020 | Apolinario | A61F 5/441 |
| 2020/0368410 | A1* | 11/2020 | Silver | A61F 13/0216 |
| 2021/0100533 | A1* | 4/2021 | Seres | A61B 5/42 |
| 2021/0244564 | A1* | 8/2021 | Jones, Jr. | A61F 5/441 |
| 2022/0133522 | A1* | 5/2022 | Chopra | A61F 5/4407 |
| | | | | 604/335 |

FOREIGN PATENT DOCUMENTS

| | | |
|---|---|---|
| WO | WO 2004/000401 | 12/2003 |
| WO | WO 2004/047695 | 6/2004 |
| WO | WO 2004/087004 | 10/2004 |
| WO | WO 2017/212263 | 12/2017 |

OTHER PUBLICATIONS

Invitation to Pay Additional Fees, Communication Relating to the Results of the Partial International Search and the Provisional Opinion dated Sep. 6, 2017 From the International Searching Authority Re. Application No. PCT/GB2017/051652. (11 Pages).

Patents Act 1977: Combined Search and Examination Report Under Sections 17 & 18(3) dated Nov. 3, 2017 From the Intellectual Property Office of the United Kingdom of Great Britain Re. Application No. GB1709071.3. (6 Pages).

Patents Act 1977: Search Report Under Section 17(5) dated Jan. 23, 2017 From the Intellectual Property Office of the United Kingdom of Great Britain Re. Application No. GB1609954.1. (4 Pages).

Patents Act 1977: Search Report Under Section 17(6) dated Oct. 6, 2017 From the Intellectual Property Office of the United Kingdom of Great Britain Re. Application No. GB1609954.1. (3 Pages).

Tucker "Stephanie Monty Designs Colostomy Bag for Intimate Moments", Dezeen, p. 1-18, Jul. 25, 2016. Photographs and Discussion of A Dressing Having A 3D Relief (in A Decorative Pattern) on the Outer Surface and Having An Anti-Bacterial Flange and Integrated Vents.

* cited by examiner

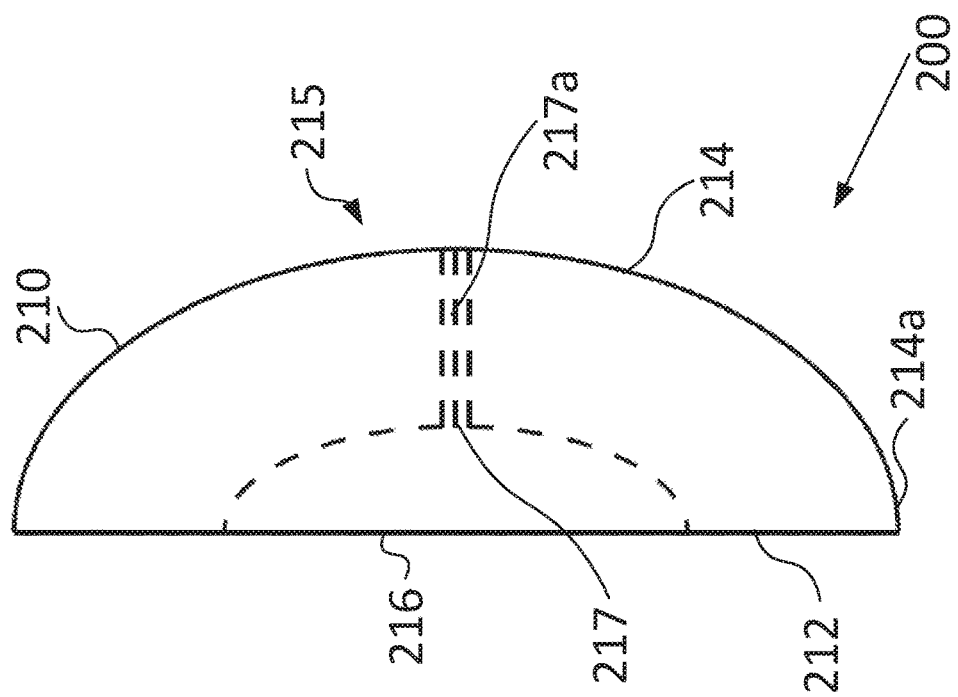
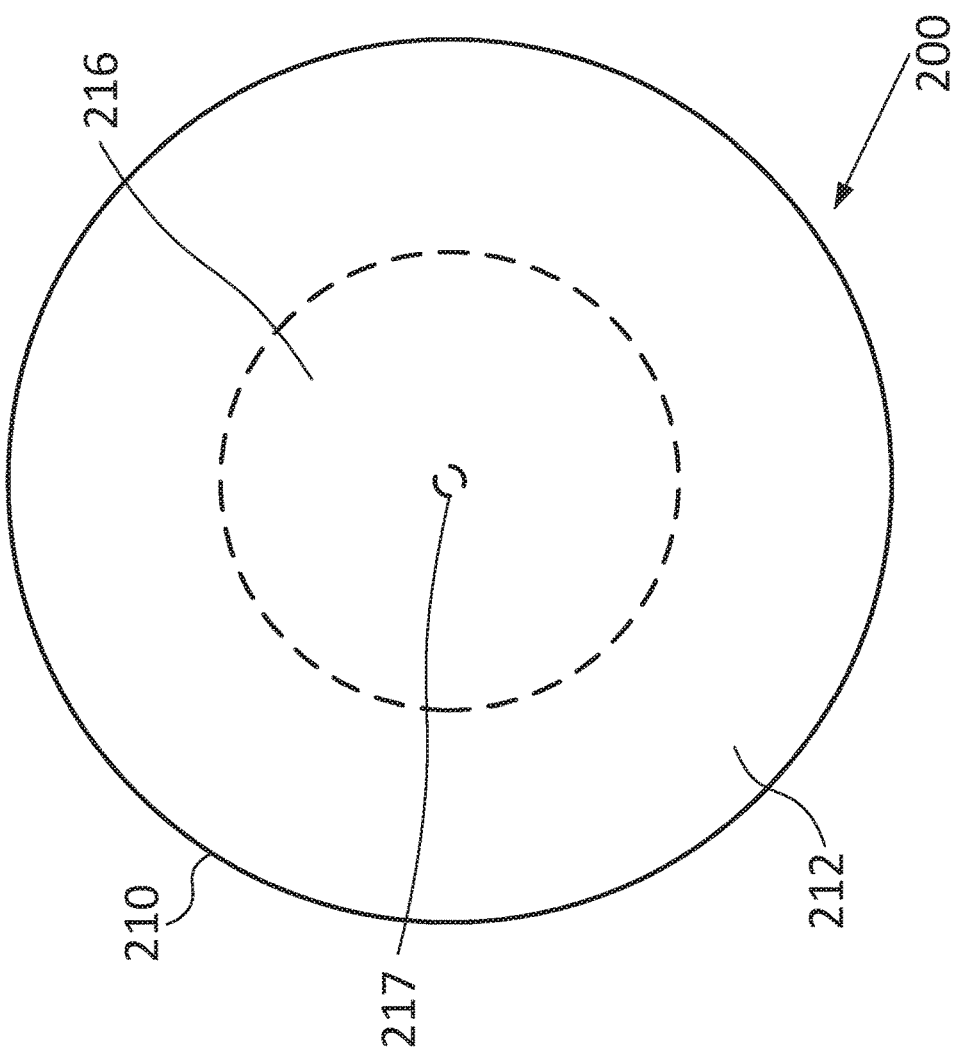
Figure 2

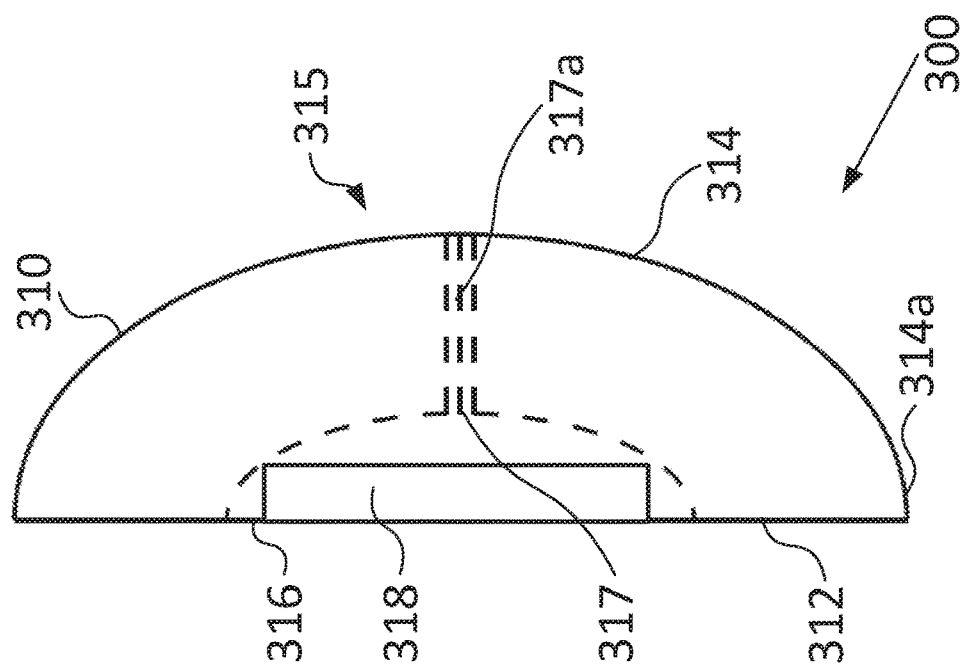
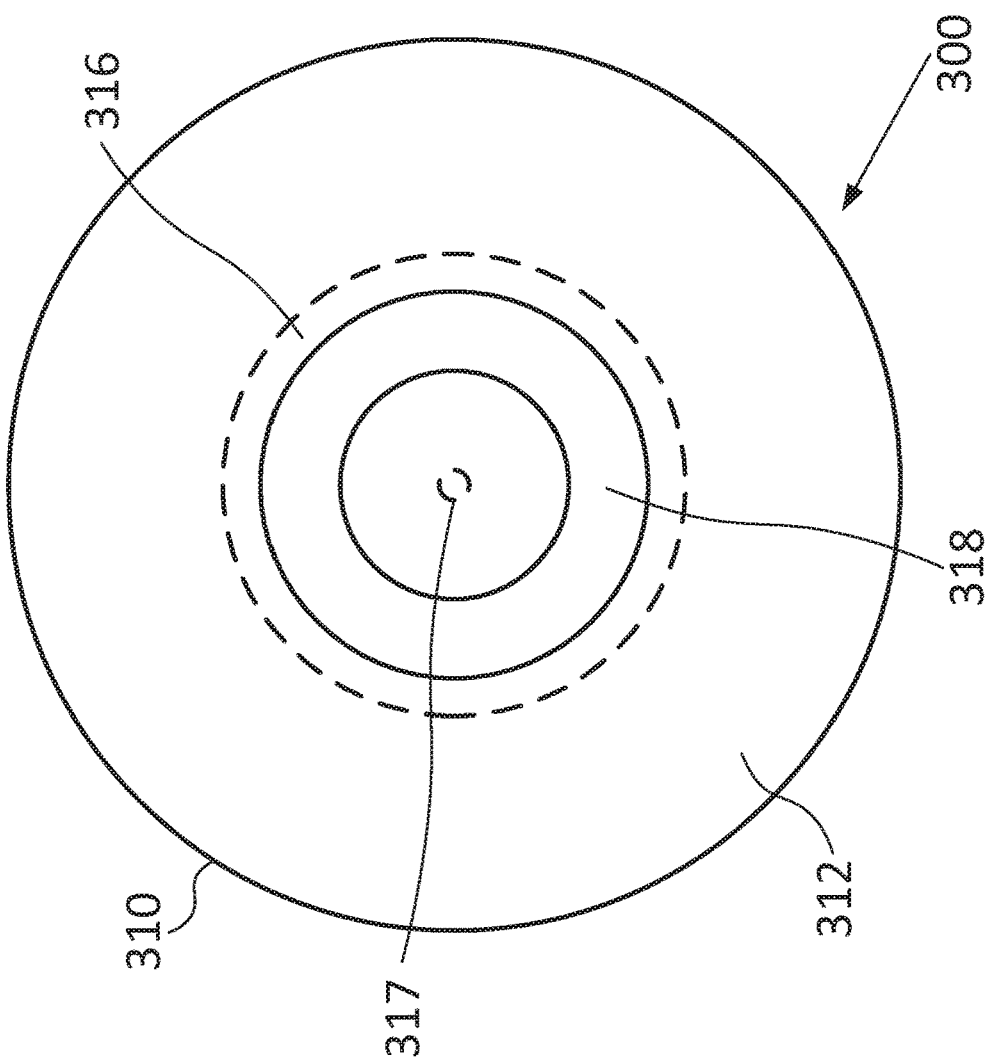
Figure 3

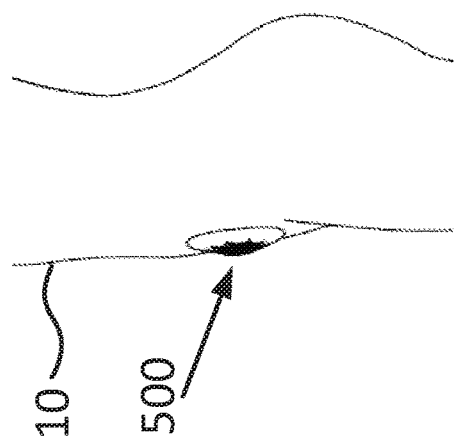
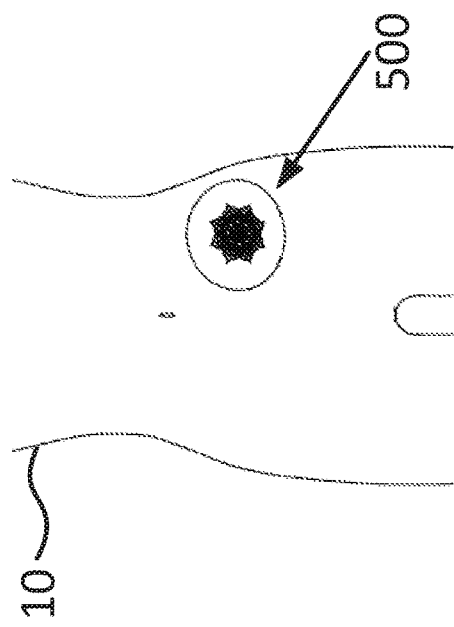
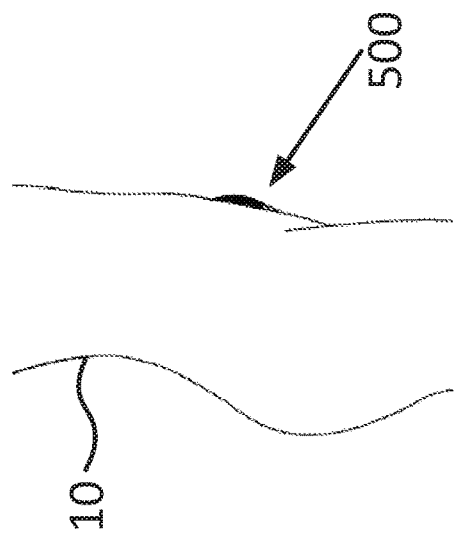

DRESSING FOR CONCEALING A STRUCTURE ON A HUMAN BODY

RELATED APPLICATIONS

This application is a continuation of PCT Patent Application No. PCT/GB2017/051652 having International filing date of Jun. 7, 2017, which claims the benefit of priority of United Kingdom Patent Application No. 1609954.1 filed on Jun. 7, 2016. The contents of which are incorporated by reference as if fully set forth herein.

FIELD AND BACKGROUND OF THE INVENTION

The present invention relates to surgical, medical or other anatomical dressings that may be applied to the human body. In particular, the invention relates to such dressings that may be applied for use in intimate situations, during bathing, or during swimming, for example to conceal a stoma or cover scarring on the human body.

Ostomy is a common surgical procedure used to create an artificial opening (or "stoma") in the body for the discharge of body wastes. Typically in such a procedure, a structure (i.e. the stoma) is formed on the surface of the abdomen to allow waste to discharge from the body.

Patients who have undergone an ostomy (known as ostomates) typically wear products such as ostomy pouches or plugs throughout the day to collect body wastes. These products can be obtrusive and uncomfortable, particularly in intimate situations or during bathing or swimming. Some ostomates experience a level of social stigma, and may feel uncomfortable in situations where their stoma or ostomy product is more likely to be noticeable.

Aspects and embodiments of the present invention are set out in the appended claims. These and other aspects and embodiments of the invention are also described herein.

SUMMARY OF THE INVENTION

According to at least one aspect described herein, there is provided a dressing for concealing a structure on a human body, the dressing comprising: a patch arranged to be placed on the body; wherein the patch has an indentation for receiving the structure so as to conceal the structure when the patch is placed on the human body.

By providing an indentation in the patch, the dressing may conceal, and preferably also disguise, a structure such as a stoma on a human body. Furthermore, such concealing may be hygienically advantageous.

The patch may comprise a first side arranged to be placed against the body and a second side arranged to face away from the first side. The indentation may be provided in the first side of the patch and may be arranged to extend towards at least a portion of the second side of the patch. The indentation may cause at least part of the second side to protrude outwardly, away from the first side, preferably wherein the peripheral edges of the patch are thinner than the portion of the patch in which the indentation is provided. At least a portion of the first side of the patch is spaced from the second side of the patch by a distance greater than the depth of the indentation. The patch may have a thickness of between 5 mm and 2 mm, and preferably at least 3 mm.

The indentation is arranged to receive a structure, for example wherein the structure is a stoma. The indentation may be substantially circular when viewed from below. Preferably, the indentation has a diameter of between 20 mm and 60 mm, and more preferably the diameter is between 25 mm and 50 mm. The indentation may be arranged so that it may be worn with an existing stoma cap or plug.

The patch may be further arranged to allow gases to be vented out of the indentation via the second side, for example wherein one or more apertures are provided on the second side of the patch. An odour resistant membrane (which is optionally absorbent) is preferably provided, which may comprise activated carbon, where the membrane is arranged in the indentation such that gases are vented through the membrane. The dressing may further comprise means for sealing the one or more apertures so as to inhibit gases from being vented from the indentation.

The dressing may further comprise an anti-bacterial component arranged to fit within the indentation. The anti-bacterial component may comprise a generally annular ring arranged to fit over the structure so as to substantially surround the structure, preferably such that the ring is in direct contact with the structure, more preferably wherein the ring is removable and disposable. The anti-bacterial component may comprise silver, such as silver nano-particles.

The dressing may further comprise means for retaining a disposable bag for receiving waste from the structure. The retaining means may be in the patch thereby to conceal the disposable bag when the patch is placed on the body. The retaining means may be a chamber within the patch, or an indentation in the patch, such as a channel. The channel may be arranged to extend around at least a part of the indentation, around a major part of the indentation, and/or the channel may be generally annular and be arranged to encircle the indentation. The retaining means is preferably provided in fluid communication with the indentation. Optionally, the dressing further comprises the disposable bag.

The patch may further comprise a three-dimensional formation arranged to face away from the body. The formation is preferably arranged to coincide with the position of a protrusion in the second side of the patch formed by the indentation and/or by the retaining means, such that the protrusion is disguised by the formation when viewed from the second side of the patch.

According to at least one aspect described herein, there is provided a dressing for concealing a structure on a human body, the dressing comprising: a patch arranged to be placed on the body; wherein a three dimensional (3D) formation is provided on at least part of the patch, said three dimensional formation being arranged to face away from the body when the patch is placed on the body so as to conceal the structure.

By providing a 3D formation on the patch, structures on the body and/or other components of the dressing may thereby be concealed. Furthermore, the patch may have an attractive appearance.

The formation may be arranged as a decorative formation and/or may have an irregular shape. The patch may be formed from a single piece of material, and may comprise silicone. At least part of the patch may be covered by a film or coating, preferably a lubricious, low coefficient of friction coating, for example but not exclusive to, MED10-6670, whereby to provide protection to that part of the patch that is not placed on the body. Alternatively or additionally, the film may be a polyurethane film.

The first side of the patch may be arranged to adhere to the body, preferably wherein the patch is arranged to adhere to skin, for example wherein an adhesive is provided on at least part of the patch. The first side may be provided with a bio-grade adhesive, preferably where the adhesive is a silicone gel adhesive. The adhesive is preferably capable of being reapplied to the body, for example such that the dressing can be reused at least once.

The patch may be arranged to have a thickness that reduces towards its peripheral edges so as to effect a generally smooth tactile transition between the patch and the body.

According to at least one aspect described herein, there is provided a method of manufacturing a dressing as described herein, comprising: obtaining one or more dimensions of a structure to be concealed; forming a patch arranged to cover an area greater than the area covered by the structure on the body; providing an indentation in the patch; wherein the indentation is configured to receive the structure when the patch is placed on the body, whereby to conceal the structure.

The indentation may be sized to correspond with the one or more dimensions of the structure thereby to receive the structure. A three-dimensional formation may be formed, or otherwise provided, on the patch, said formation having one or more features for disguising the indentation. Preferably, the features of the formation are specified by a user of the patch.

According to at least one aspect described herein there is provided a method of manufacturing a dressing as described herein comprising: forming a patch having provided thereon a three-dimensional (3D) formation; wherein the formation is arranged to face away from the body.

Preferably, the patch is formed from a single piece of material, for example silicone. The three-dimensional formation (or shape/design) may be provided by the intended user of the dressing and/or the three-dimensional formation may be created from a two-dimensional shape or design provided by the intended user of the dressing, for example. The three dimensional formation may alternatively be created from a range of designs provided by the manufacturer.

An adhesive may be provided on at least part of the patch that is arranged to be placed on the body. A protective film or coating may be provided over at least part of the patch, preferably said at least part of the patch that is arranged to face away from the body.

According to at least one aspect described herein, there is provided a machine-readable map, or machine-readable instructions, configured to enable a 3D printer (or any printer or manufacturing device/system) to manufacture at least part of a dressing or mould as herein described.

The invention extends to a dressing and/or a method of manufacturing a dressing substantially as described herein and shown in the accompanying figures.

As used herein, the term 'patch' preferably connotes a piece of material that may be used to cover part of a human body, for example in a medical context to cover a scar, wound or stoma.

As used herein, the term 'structure' preferably connotes a protrusion or otherwise deformed area on a human body resulting from a previous wound or surgical procedure, such as scar tissue or a stoma.

As used herein, the term 'indentation' preferably connotes a recess, hollow, depression, scoop, dent or notch, for example.

As used herein, the term 'medical-grade' preferably connotes materials having met certain necessary standards relating to biocompatibility during manufacture, such as toxicity testing.

As used herein, the term 'anti-bacterial' preferably connotes being active against bacteria, for example destroying, inhibiting or suppressing the growth or reproduction of bacteria.

As used herein, the term 'conceal' preferably connotes to cover, disguise, obscure, screen, mask or camouflage, for example.

Any apparatus feature as described herein may also be provided as a method feature, and vice versa. Furthermore, any feature in a particular aspect may be provided independently and/or applied to other aspects, in any appropriate combination.

It should also be appreciated that particular combinations of the various features described and defined in any aspects can be implemented and/or supplied and/or used independently.

As used herein, means plus function features may be expressed alternatively in terms of their corresponding structure.

BRIEF DESCRIPTION OF THE SEVERAL VIEWS OF THE DRAWINGS

The present invention will now be described, purely by way of example, with reference to the accompanying figures, in which:

FIG. 2 shows schematic rear and side views of a dressing comprising a patch having a vent;

FIG. 3 shows schematic rear and side views of a dressing comprising a patch and an anti-bacterial component;

FIGS. 7a, 7b, 7c, and 7d show the dressing of FIG. 5 applied to the body of a user;

DESCRIPTION OF SPECIFIC EMBODIMENTS OF THE INVENTION

Figure 1:
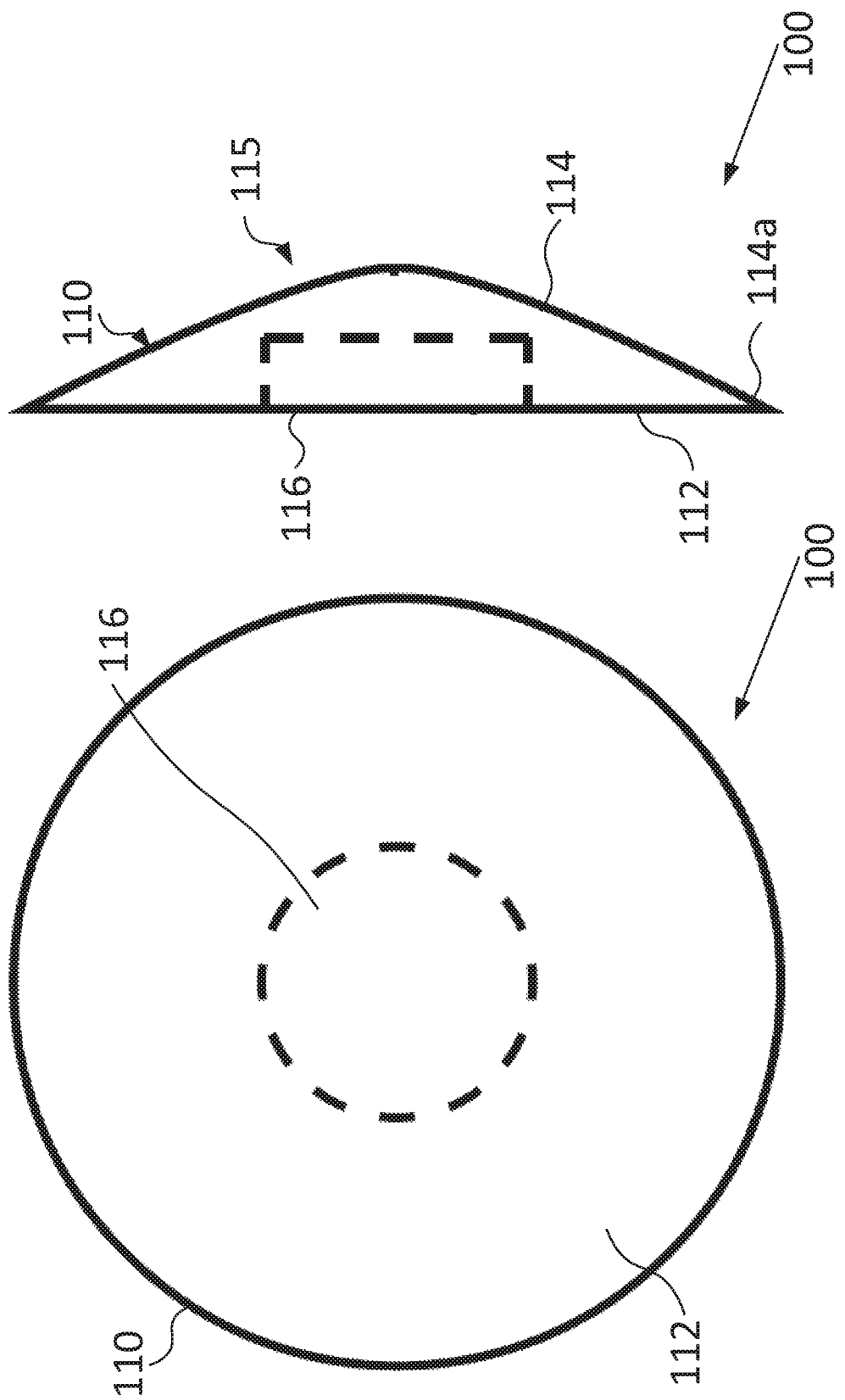
FIG. 1 shows schematic rear and side views of a dressing in one example of the present invention.

FIG. 1 shows schematic rear and side views of an exemplary dressing 100 in the form of a "patch" 110. The patch comprises a first side 112 and a second side 114. The first side 112 is arranged to be placed on the body of a user, and the second side 114 is arranged to face away from the first side 112. As such, the first and second sides may be considered to be opposing. At least part of the second side 114 is spaced away from the first side 112, such that the patch 110 protrudes away from the patient's skin.

In its simplest form, the patch 110 may comprise a single piece of material, such as a cast silicone piece. The patch 110 should be arranged to be capable of being placed on the body of a user, preferably such that it adheres to the skin of a user, as will be described later on.

Figure 4:
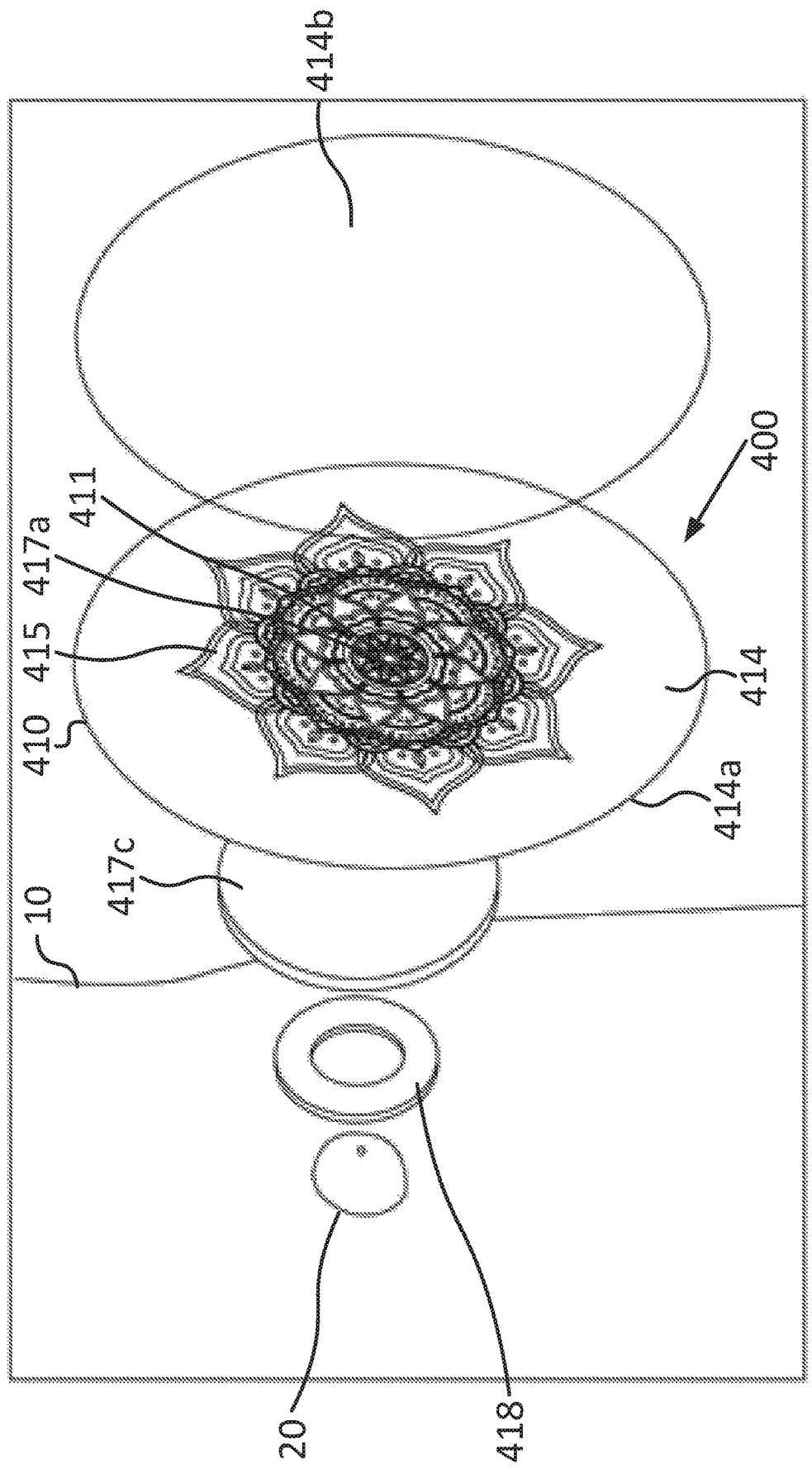
FIG. 4 shows an exploded view of another example of a dressing during application.

The first side is arranged to receive a structure, such as a stoma 20 (as illustrated in FIG. 4) and may therefore comprise an indentation 116, for example a recess or notch. The indentation 116 is circular to accommodate the stoma, and the diameter and the depth of the indentation 116 may be selected in dependence on the size of the stoma 20. Alternatively, a range of standard diameters of indentation 116 may be available, which may range from 20 mm to 60 mm, or more preferably 25 mm to 50 mm, for example. A non-circular indentation 116 may alternatively be used if the patient has an irregular-shaped stoma 20. The indentation 116 allows the patch to be applied over a stoma without pressing on the stoma, allowing the stoma to be concealed and hence disguised by the dressing. Preferably, the depth of the indentation 116 is arranged to provide a gap of at least 3 mm, between the distal end of the stoma 20 and the patch 110. The part of the patch coinciding with the indentation may have a thickness of between 5 mm and 2 mm, and preferably at least 3 mm.

The patch 110 can be used to cover a stoma hygienically without being used in combination with an ostomy product or leaving the stoma exposed, either of which are required when conventional disguising products (such as specialist underwear) are used. Advantageously, the dressing is much less obtrusive than a conventional ostomy product and may have significant aesthetic appeal.

An adhesive is, ideally, used to adhere the patch 110 to a patient's skin. Preferably, the adhesive is provided evenly across the first side 112, (preferably avoiding the indentation). It may alternatively be provided as a separate substrate, as described below. The adhesive alternatively is preferably a medical grade and bio-compatible adhesive, and may be selected so as to have a strong bond with the skin so as prevent the patch coming loose or peeling. The strength of the bond should however not be so strong as to cause significant trauma or skin maceration when the patch is removed. The adhesive is preferably hypoallergenic and/or should not substantially affect skin pH or moisture levels. A pressure-sensitive adhesive may be used, wherein the adhesive may be applied to the patch 110 using pressure sensitive adhesive (PSA) heat lamination methods. Preferably, the adhesive provides sufficient residual adhesion to allow the patch to be reused at least once following removal. The first side 112 of the patch 110 may be provided on a release liner, which may be removed to allow the patch to be applied. A silicone gel adhesive is an example of a possible adhesive that could be used, which is preferred due to its high breathability and flexibility.

The second side 114 of the patch 110 comprises a three-dimensional formation 115, which in FIG. 1 is represented as a surface with a raised profile. The second side 114 may be arranged to reduce in thickness towards its edges 114a, such that the edges of the second side 114 form an acute angle with the edges of the first side 112. This allows the patch to blend unobtrusively into the skin and reduces the possibility of the patch accidentally being lifted off. The patch may be arranged to be as thin as possible, but will be limited by the size of the structure being concealed (and hence the depth of the indentation 116). In general, the middle (and thickest) portion of the patch has a thickness of between 10 mm and 30 mm, and tapers to a thickness of around 2 mm-3 mm on the edges 114a.

Referring to FIG. 2, in which corresponding reference numerals have been used to show corresponding parts, schematic rear and side views of another exemplary dressing 200 comprising a patch 210 and having a vent 217 are shown. The vent 217 allows gas to escape from a stoma via indentation 216. One or more ventilation apertures 217a (which may be, for example, approximately 1.5 mm in diameter) may be provided from the vent 217 to the second side 214 of the dressing 200 to allow gases to escape. The vent 217 may be implemented in various ways, as will be described by way of example below. The dressing 200 is otherwise identical to the dressing 100 as previously described.

FIG. 3 shows schematic rear and side views of another exemplary dressing 200 comprising a patch 310 and an anti-bacterial component 318. Corresponding reference numerals have been used to show corresponding parts. The anti-bacterial component 318 is arranged in an indentation 315 on the first side 312 of the patch 310, which is otherwise substantially similar to the dressing 200 previously described. The anti-bacterial component 318 may be substantially annular or "ring-shaped" and is ideally shaped to fit around the stoma so as to surround the stoma and also to be in contact with the skin around the stoma 20 (which may be referred to as 'peristomal skin'), so as to protect against infection. The anti-bacterial component 318 is arranged to fit closely around the stoma, being preferably spaced no further than 1 mm away from the sides of the stoma. This inhibits leakage of the waste from the stoma onto the peristomal skin. The anti-bacterial component 318 may be provided with adhesive to adhere to the skin and/or to the patch 310.

The anti-bacterial component 318 is preferably made of a soft and/or flexible material to avoid irritating the peristomal skin. The anti-bacterial component 318 also preferably comprises silver being arranged to act as a bactericide. For example, the anti-bacterial component 318 may be made of silicone having diffused silver nanoparticles. Experimental anti-bacterial components 318 comprising 8-10 nm silver particles at 99.9% purity have been shown to kill *E. coli* colonies placed in contact with the anti-bacterial components 318 at a much faster rate than colonies placed in contact with a control sample. Infectious conditions of the peristomal skin are common, and can significantly affect a stoma patient's quality of life. The provision of the anti-bacterial component 318 helps to reduce the likelihood of such infections occurring. Prior art ostomy devices do not contain an anti-bacterial component.

The anti-bacterial component 318 may be disposable, and may be removable such that the dressing 300 may be worn with or without it. The anti-bacterial component 318 may be arranged to cover at least 5-20% of the stoma, and may therefore have a thickness of between 1-10 mm, or more preferably between 2-3 mm, for example, preferably wherein the anti-bacterial component 318 is arranged to fit securely (or tightly) around the base of the stoma. The anti-bacterial component 318 may optionally be located in a recess provided at the opening of the indentation 316, or alternatively may fit closely between the walls of the indentation 316.

FIG. 4 shows an exploded view of an exemplary dressing 400 comprising a patch 410 prior to application to the abdomen 10 of a user. Corresponding reference numerals have been used to show corresponding parts. The dressing 400 includes an anti-bacterial component 418 arranged to fit over a stoma 20. The second side 414 of the patch 410 has a three-dimensional formation 415, which may be arranged as a decorative design. For example, a mandala design may be used. The formation 415 may comprise decorative elements extending above a substantially flat or planar base layer provided by the second side 414. The formation 415, and therefore the dressing 400, preferably extends over a much wider area than the stoma 20. For example, a stoma 20 having a diameter of 20 mm may require a dressing having a minimum width/diameter of at least 110 mm; a stoma 20 having a diameter of 50 mm may require a dressing having a minimum width/diameter of at least 130 mm (e.g. a minimum width in any direction across the dressing, or minimum diameter where the dressing is generally circular in shape). The size and placement of the dressing 400 may be chosen to promote the ability of the user to move freely without the dressing coming away from the body.

A bulbous or otherwise raised element 411 of the formation 415 may optionally be used to conceal the indentation 416 for the stoma 20. In the dressing 400 shown in FIG. 4, the raised element 411 (and therefore the indentation 416) is provided centrally in the formation 415 and dressing 400. The raised element 211 and/or the indentation 416 may alternatively be provided off-centre. The raised element 311 may be incorporated into the formation 415 in a decorative way, for example by being incorporated into the formation 415 as the bulb of a flower or as the centre of a mandala design, as shown in FIG. 4. The raised element 411 concealing the indentation 416 may be the part of the formation 415 that is furthest from the skin, so as to minimise the thickness of the rest of the dressing 400.

The second side 414 of the patch 410 may be coated with a film 414b (shown in FIG. 4 as a separate layer), such as a polyurethane film, to protect the patch, to allow it to be washable and/or to improve the surface finish and/or texture of the patch 410. The film is preferably breathable and presents a barrier to bacteria. An example of a suitable film is AU25 or EU50 film made by Delstar Technologies®. In an alternative, a lubricious coating with a low-coefficient of friction may be used, such as MED10-6670 made by NuSil Technology®.

In the dressing shown in FIG. 4, venting may be controlled by an odour absorbent membrane 417c, which is arranged to fit into the indentation 416 to control the flow of any gases out of the indentation 416 via one or more ventilation apertures 417a. In this example, the odour absorbent membrane 417c is provided as part of a film, and may be laminated or heat welded into polyurethane film, for example. The membrane 417c comprises activated carbon. The ventilation apertures 417a are preferably arranged unobtrusively within the formation 415. For example, in the dressing shown in FIG. 4, the ventilation apertures 417a are incorporated in a substantially annular arrangement in the raised element 411.

Figure 5:
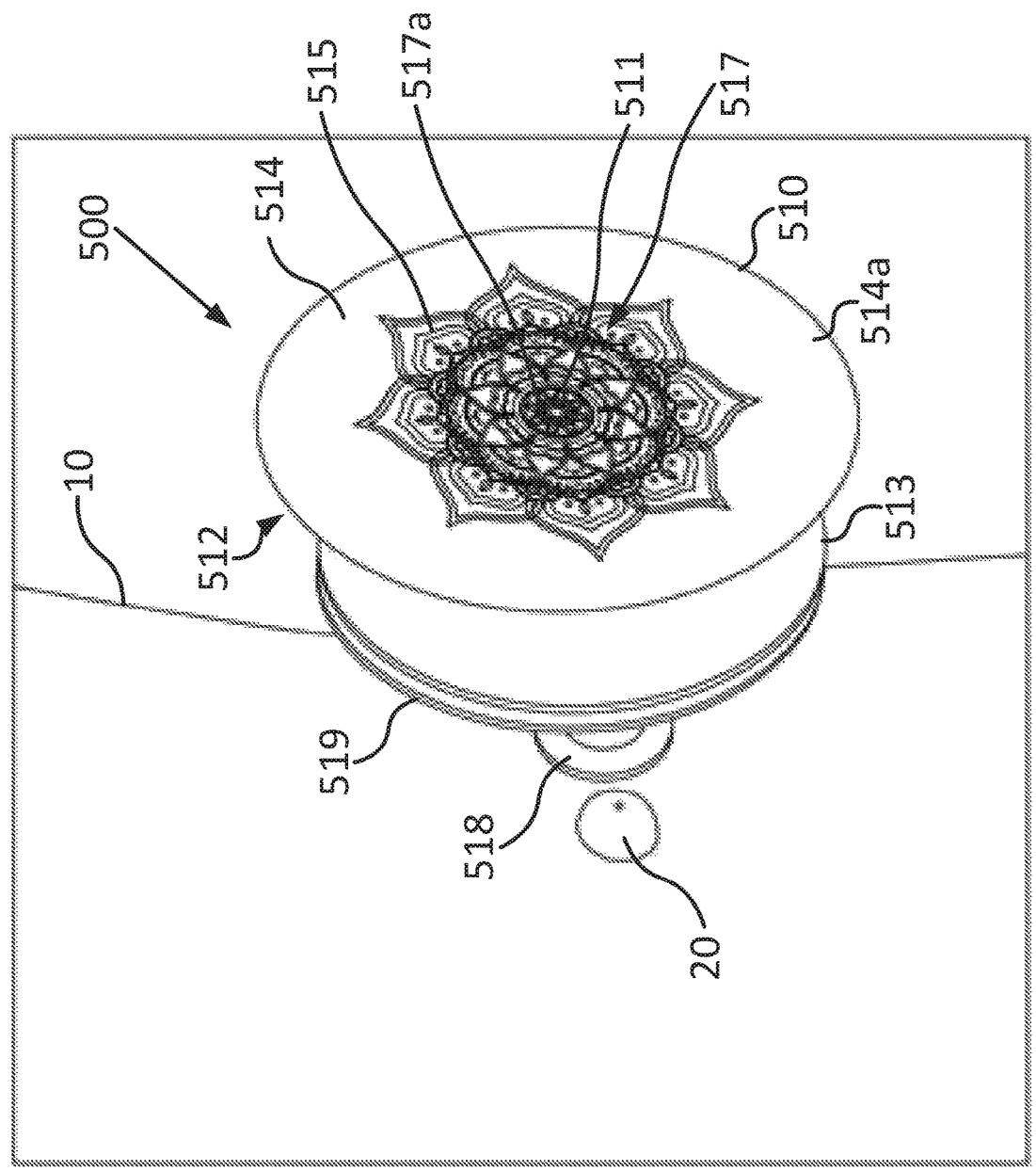
FIG. 5 shows an exploded view of another example of a dressing arranged to conceal a stoma.

FIG. 5 shows an exploded view of another exemplary embodiment of a dressing 500 for covering a stoma 20. Corresponding reference numerals have been used to show corresponding parts. In FIG. 5, the adhesive is shown as a separate layer 513 located between a first side 512 of the patch 510 and a release liner 519. The adhesive is provided in a substantially ring-shaped layer 513 such that is no adhesive provided around the indentation 516. The release liner 519 may be manufactured with the adhesive before the adhesive is bonded to the patch 510. To apply the dressing 500, the release liner 519 may be pulled back to expose the adhesive.

In the dressing 500, a removable vent cap 517b (not shown in FIG. 5) may optionally be provided over one or more ventilation apertures 517a and/or a vent 517 (indicated in FIG. 5). The dressing 500 may otherwise be substantially functionally identical to the dressing 400 described in relation to FIG. 4. The vent cap 517b may be removed to expose the vent 517 and allow gas to escape from the indentation 516. Preferably, the vent cap 517b seals the vent 517 when fitted. The provision of a vent cap 517b may allow for a larger vent 517 to be used.

Figure 6:
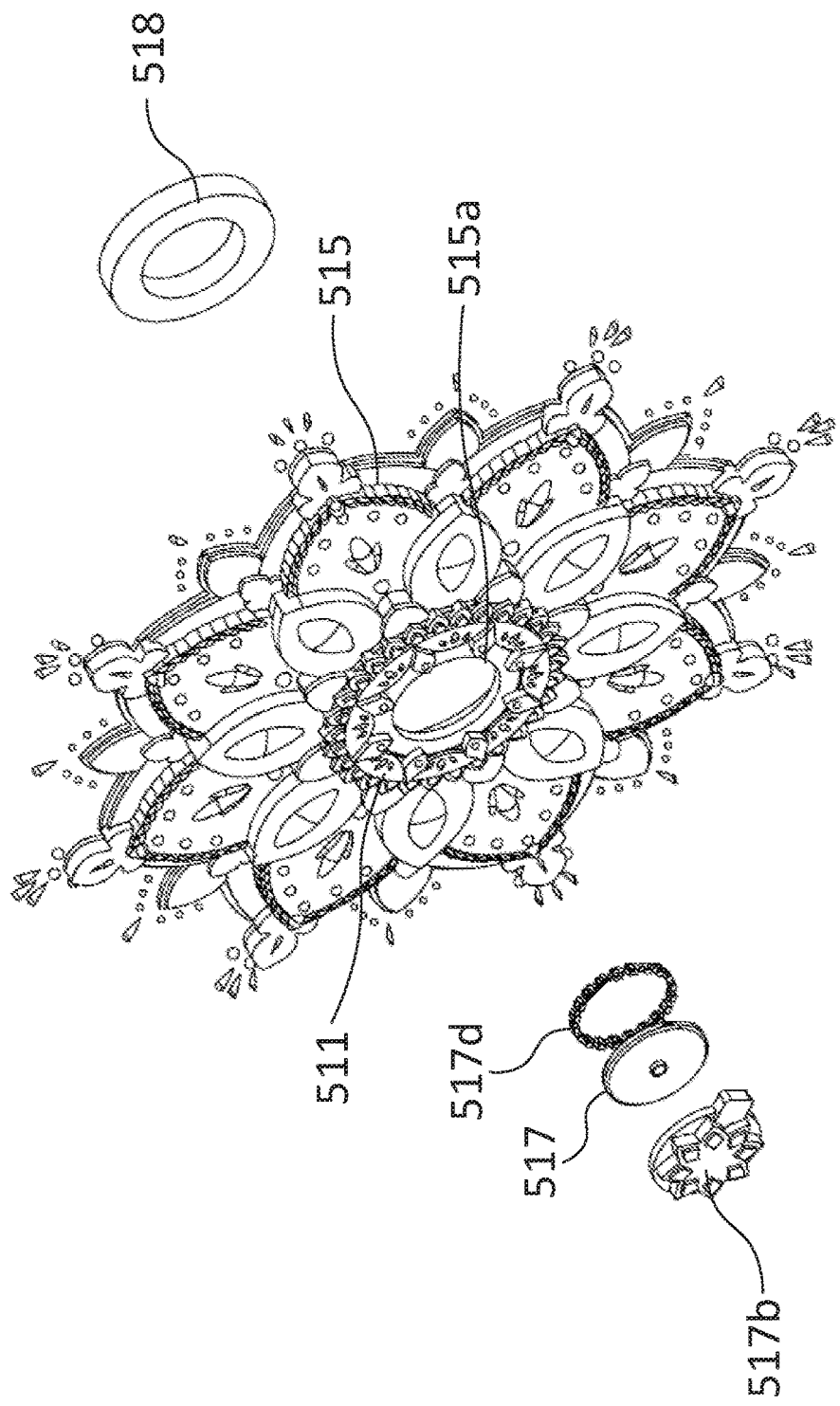
FIG. 6 shows an exploded view of several of the parts of the dressing of FIG. 5.
Figure 7A:
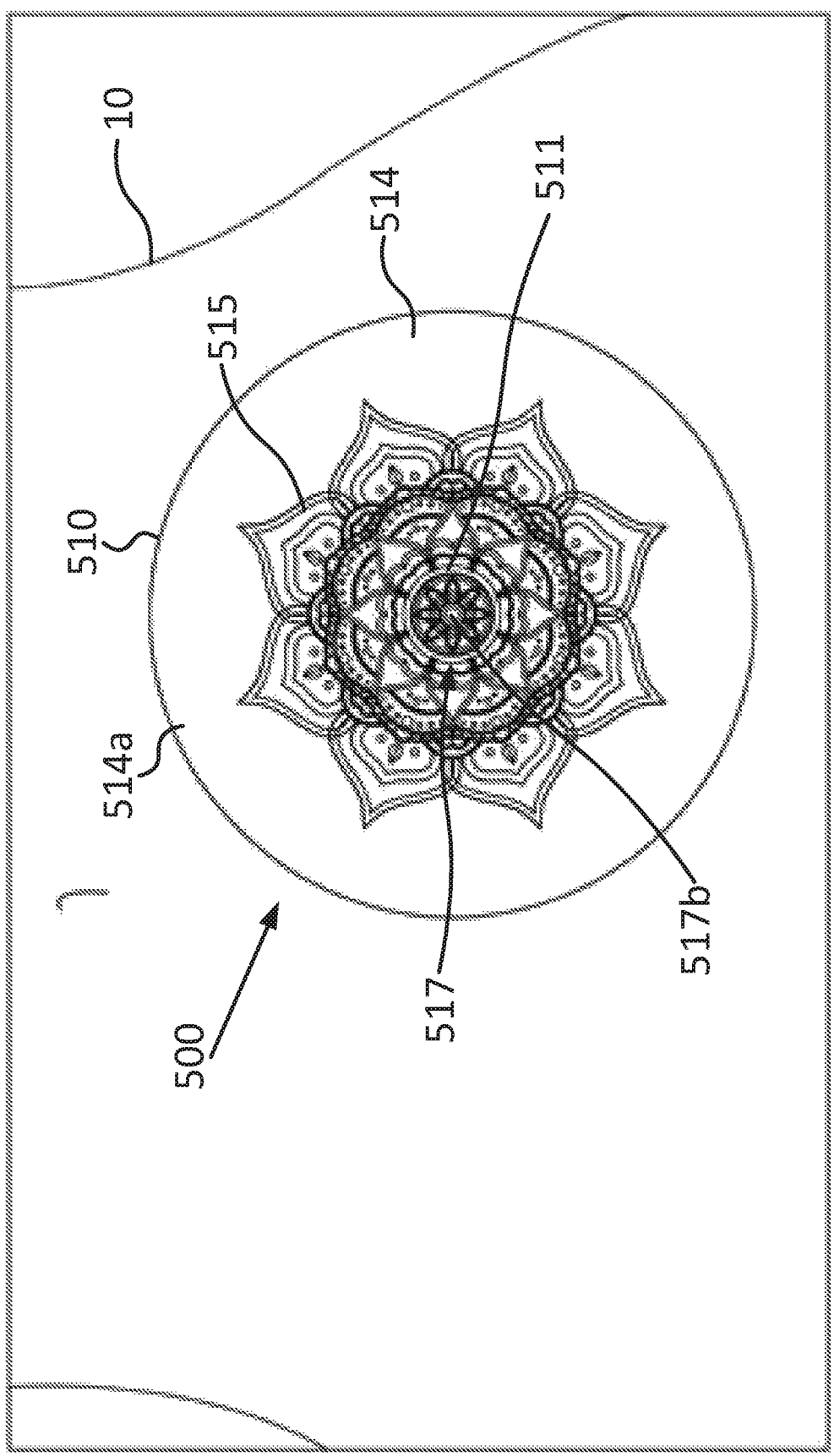

FIG. 6 shows an exploded view of several of the parts of dressing 500, where the vent cap 517b is shown. An exemplary vent 517 for use in an ostomy pouch may be used with the dressing 500, such as the Osto EZ Vent® venting device. The vent 517 can be provided in combination with an odour absorbent membrane (not shown) and/or a mesh filter 517d which may be located beneath the vent 517, being sealed by the vent cap 517b. The vent cap 517b is preferably arranged to be accommodated unobtrusively as part of a formation 515. In the dressing 500, the vent cap 517b is arranged to fit over a raised element 511, which contains the ventilation apertures 517a on which the vent 517 is located.

FIG. 7a-d shows the dressing 500 of FIG. 5 applied to the abdomen 10 of a user thereby concealing the stoma 20.

Figure 8A:
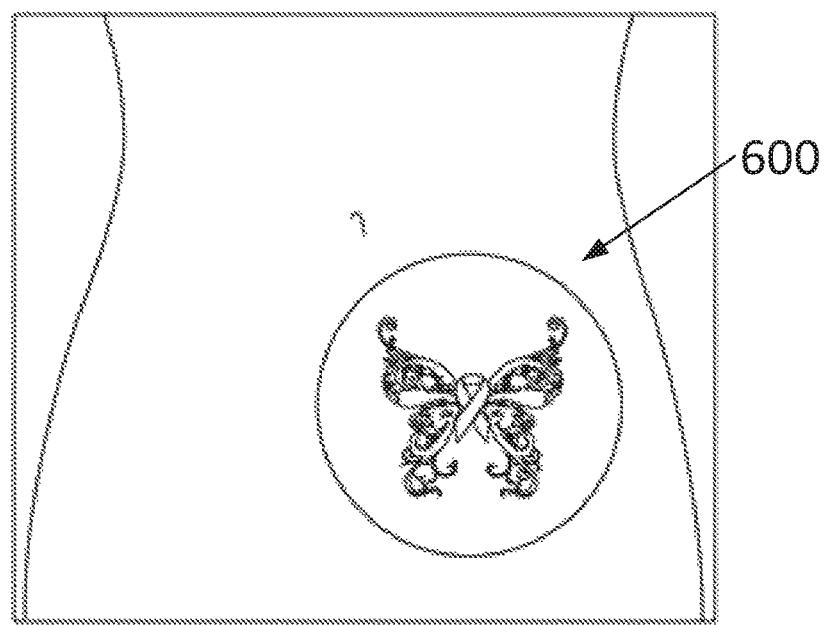
FIGS. 8a, 8b, 8c, 8d, 8e, and 8f show different examples of possible formations arranged on dressings.

FIGS. 8a-8f show different dressings 600, 700, 800, 900 with alternative exemplary formations 615, 715, 815, 915. Corresponding reference numerals have been used to show corresponding parts. As these figures show, a dressing may have a non-circular shape. As FIG. 8a shows, a formation 615 may comprise a single three-dimensional shape provided over the second side of the patch as an alternative to the second side providing a base layer. In this case, a raised section containing an indentation may be unobtrusively provided in part of the shape.

Figure 8B:
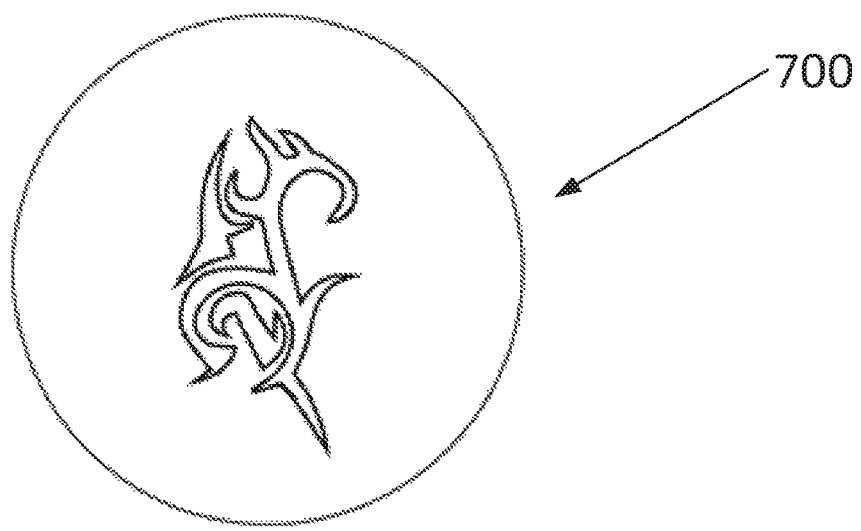

FIG. 8b shows a dressing 700 with a more protruding profile, which may be suitable for larger stomas.

Figure 8C:
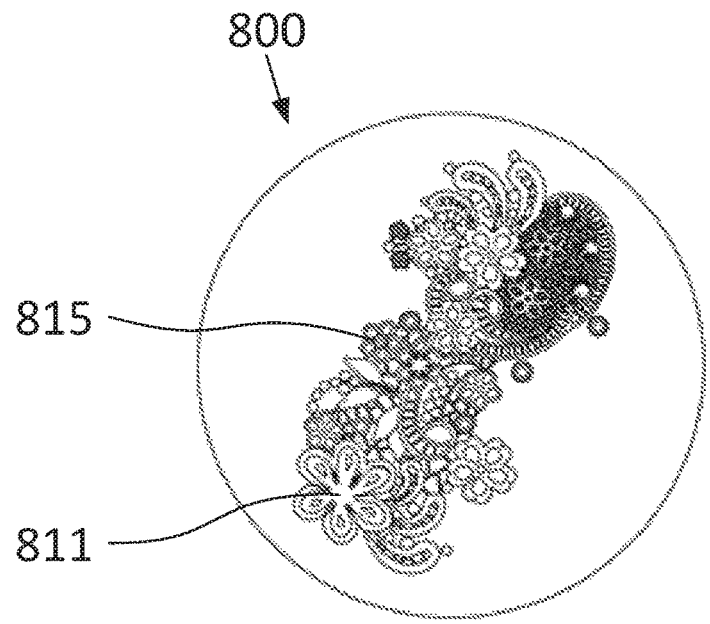
Figure 8D:
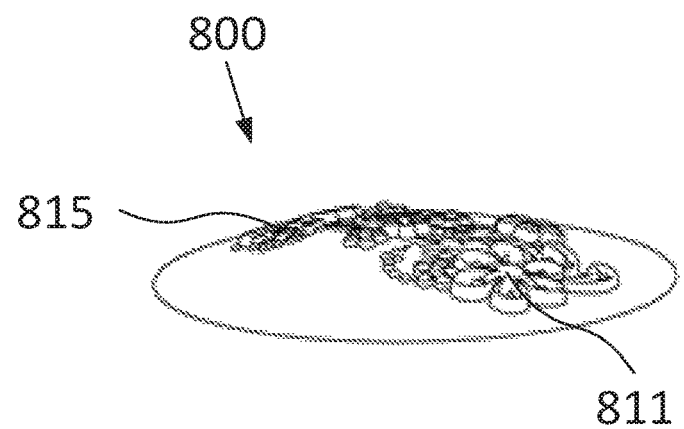
Figure 8E:
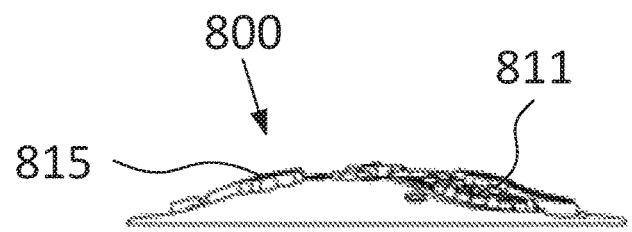
Figure 8F:
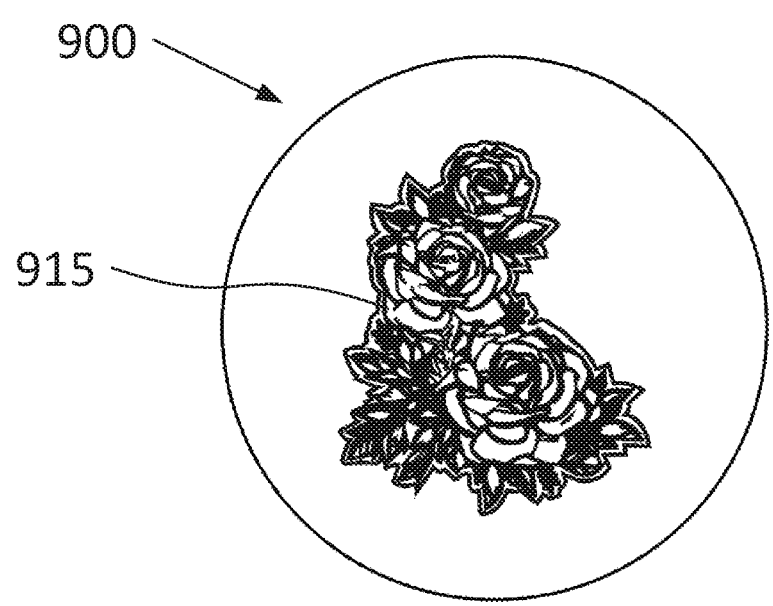

The exemplary formation 815 shown in FIG. 8c comprises a raised section 811, which may optionally be used to conceal an indentation. If provided, such a raised section 811 may be provided off-centre in the formation 815 and may be surrounded with various decorative elements in a similar theme, thereby to improve the concealment of the raised section (and thereby improve the concealment of the stoma). The colour of a patch may optionally be varied, for example to match a patient's skin tone. FIGS. 8d and 8e show perspective and side views of the dressing 800 of FIG. 8c. FIG. 8f shows a dressing 9000 having a further formation 915.

As mentioned, the patch preferably comprises silicone, and preferably a single cast piece of silicone. A bio-grade silicone should be used, such as "silicone liquid rubber" supplied by Dow Corning® or Scapa® or Nusil Technology®.

Figure 9:
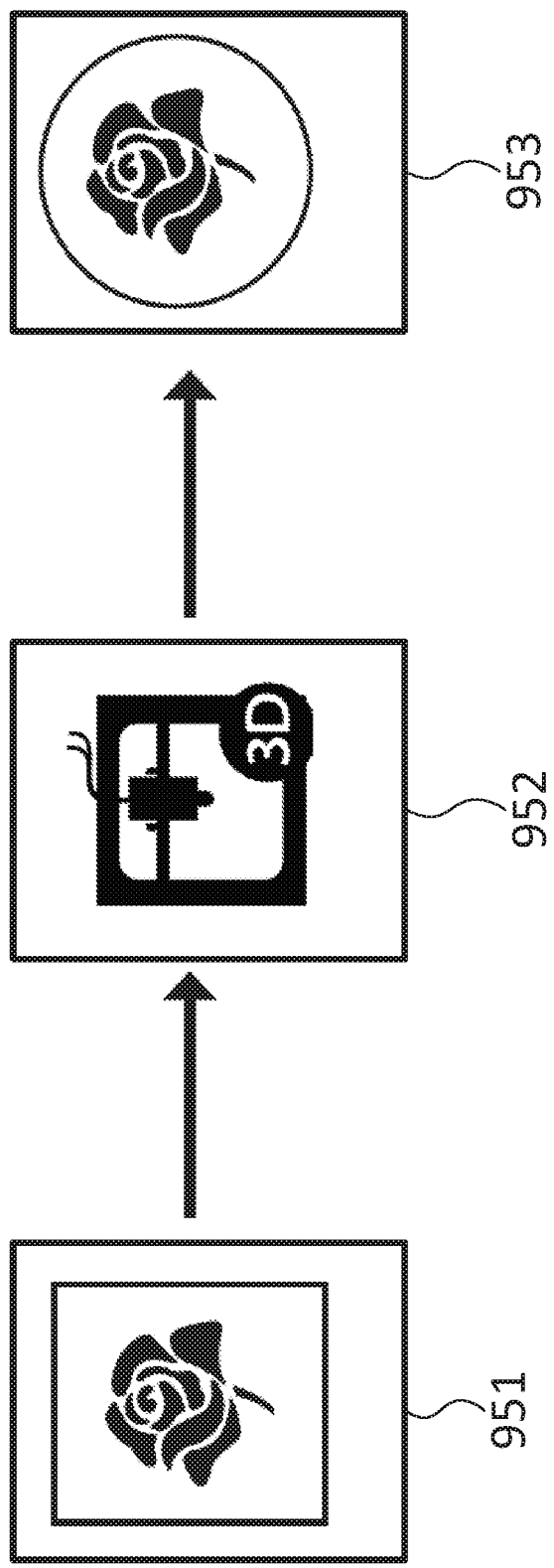
FIG. 9 shows a schematic flow diagram of a method of manufacturing a dressing.

FIG. 9 shows a schematic flow diagram of a method of manufacturing a dressing. The patch may be customised based on a preferred formation (optionally specified by a user) and the dimensions of the user's stoma. In step 951, a 2D drawing of a preferred design or formation may be provided by the user. In step 952, the 2D design may be drawn up in 3D, for example using a CAD package, and may be modified to incorporate a suitable indentation for a stoma. In step 953, a mould for the formation may be rapid prototyped (for example, by being 3D printed), and used to cast silicone, producing a patch having a formation corresponding to the 3D design. In an alternative, the patient may choose a formation from a range of existing designs. The bactericidal component may be cast in a similar way, with additional processing steps of introducing and dispersing the silver nanoparticles. For hygiene, the patch (and/or optionally the mould) are manufactured in a clean room.

The colour of the patch may be controlled using dyes or additives introduced into the silicone during casting. The colour may be selected in dependence on the formation used.

For example, a black colour may be used in tattoo-like formations, and a colour matching skin tone may be chose in minimalistic formations.

Figure 10:
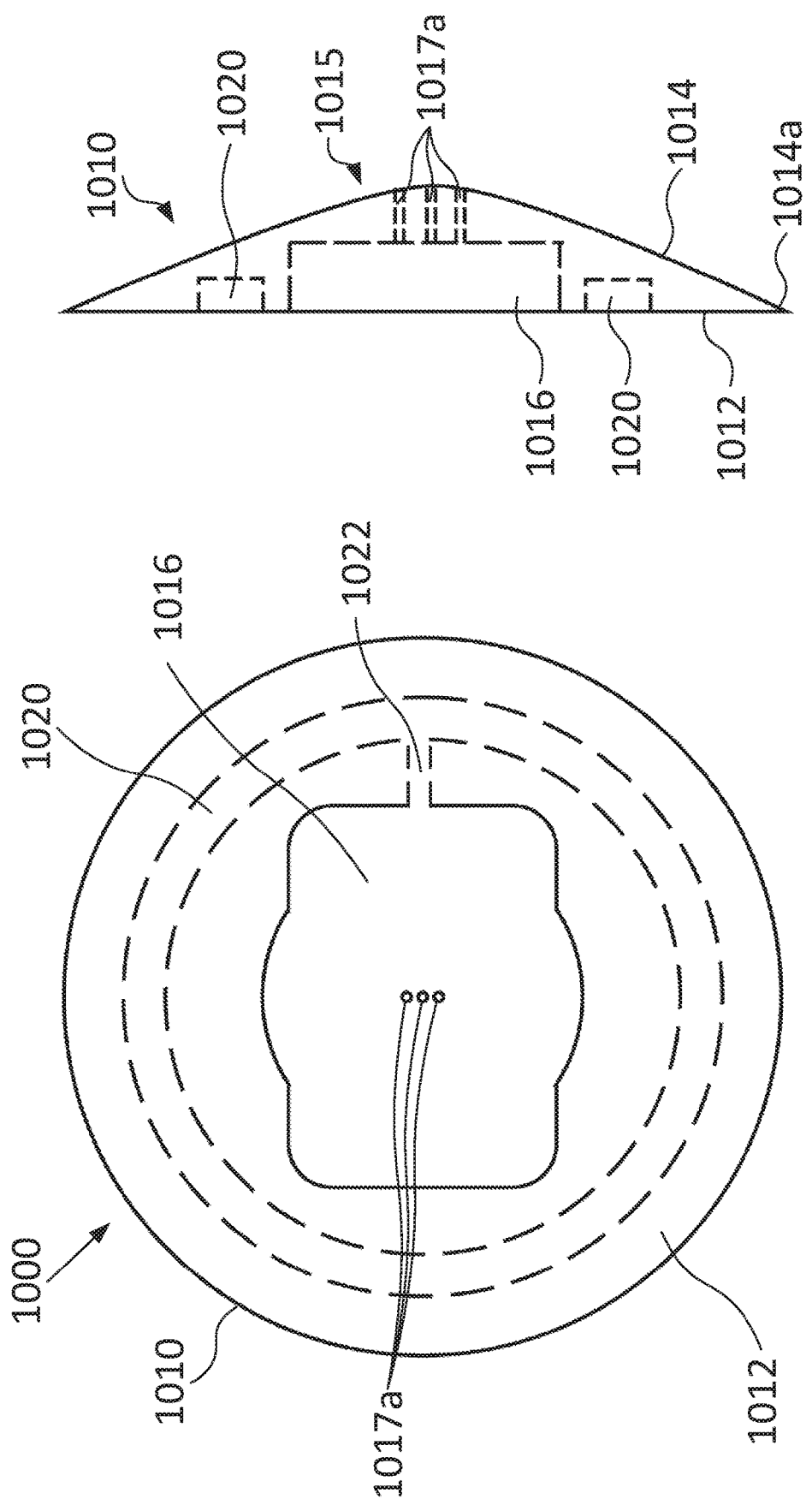
FIG. 10 shows schematic rear and side views of a dressing comprising a channel.

FIG. 10, in which corresponding reference numerals have been used to show corresponding parts, shows schematic rear and side views of a further example of a dressing 1000. The dressing 1000 includes a patch 1010 having a relatively large indentation 1016, which has a generally rectangular shape with opposing circular segments on either side of a long edge of the rectangular shape. The size and shape of the indentation allow products applied to the stoma (such as a covering or a separate venting device) to be easily fitted into the indentation, as well as the stoma itself. In the dressing 1000, the vent is formed from three ventilation apertures 1017*a*, which extend from a centre of the indentation 1016 to a second side 1014 of the dressing.

The patch 1010 further comprises a further indentation (or recess) shaped as a generally circular channel 1020 in the first side 1012, where the channel extends around the indentation 1016 so as to surround the indentation. The channel is recessed into the first side, and is arranged to retain a bag (or tube) for receiving waste (i.e. faecal output) from a stoma in the indentation. A fluid connection 1022 is provided from the indentation to the channel to allow waste to flow into the channel, where the fluid connection is recessed into the first side.

The bag (not shown) is generally tubular in shape and is arranged generally to conform to the shape of the channel. Preferably, the bag extends throughout a major part of the channel 1020. This may extend into the indentation 1016 (via the fluid connection 1022) proximate the stoma to receive waste, or alternatively it may be engaged with a separate product (such a venting device) engaged with the stoma (which is received into the indentation as well as the stoma). The bag retained in the channel is removable and disposable, where a user can remove the dressing 1000 and extract the bag or tube from the channel 1020 manually. The bag accommodates at least 50 ml of waste, and preferably more than 60 ml of waste.

Figure 11:
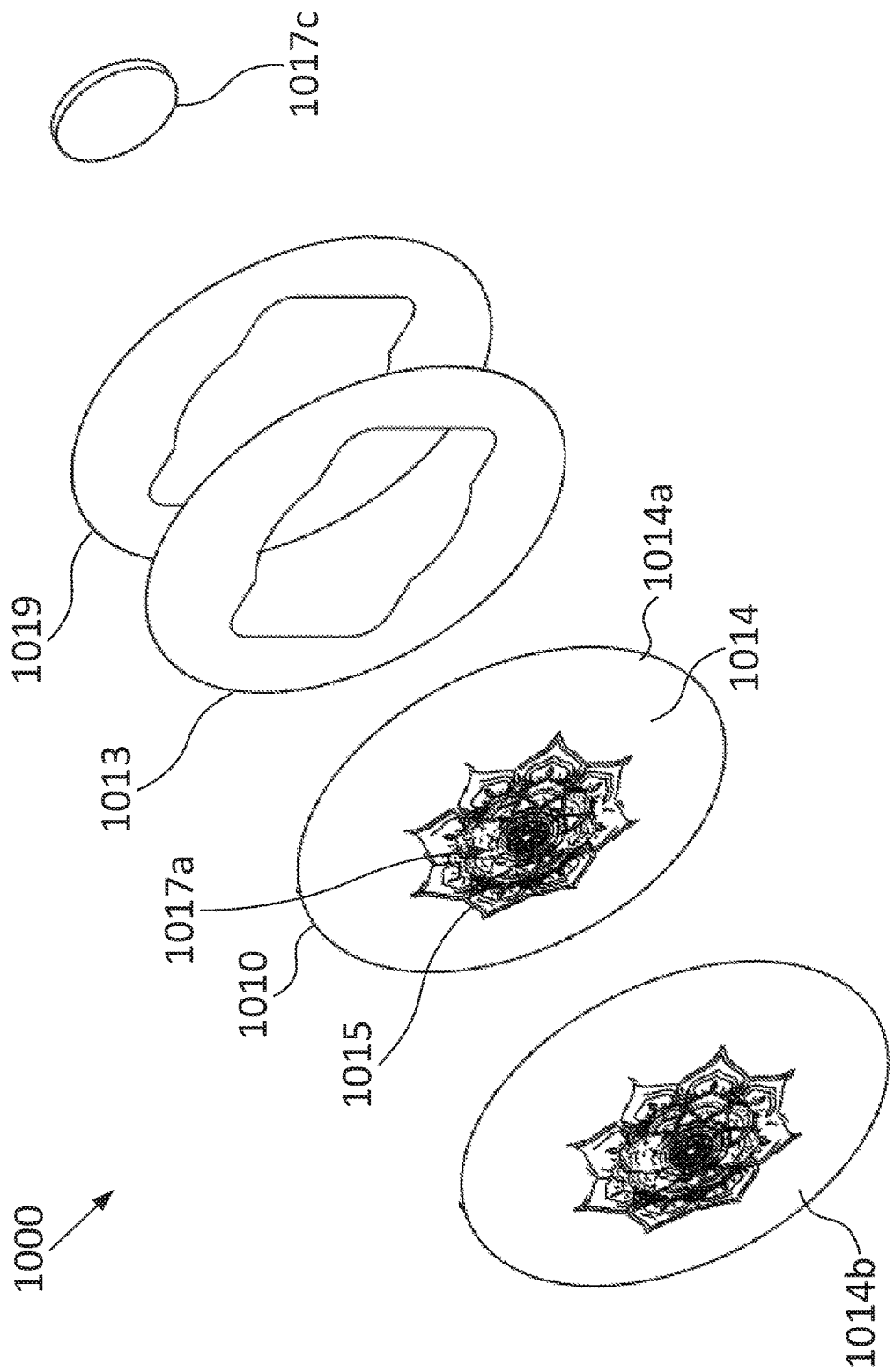
FIG. 11 shows an exploded view of the dressing of FIG. 10.

FIG. 11 shows an exploded view of the dressing 1000 of FIG. 10. Corresponding reference numerals have been used to show corresponding parts. As previously described, the patch 1010 is formed from silicone and includes a three-dimensional formation 1015 on a second side 1014. The second side is covered by a spray coating 1014*b* (which does not seal the ventilation apertures 1017*a*) for protection and to improve the surface finish and appearance of the dressing. The first side 1012 of the patch is covered with a layer of silicone adhesive 1013 to adhere the patch 1010 to a human body. The adhesive is preferably reusable and waterproof. The adhesive is provided with a release liner 1019 for protecting the adhesive until use. Neither the adhesive nor the release liner extend over the indentation. An odour absorbent membrane 1017*c* is arranged to fit into the indentation so as to extend over the ventilation apertures 1017*a*. The membrane 1017*c* consists of a membrane of activated carbon with a protective coating or laminate. An antibacterial component (as previously described) may optionally also be used with the dressing 1000.

It will be appreciated that the channel 1020 may be implemented in a variety of different ways, for example as a helical channel extending away from the indentation 1016 (in which case there is no separate fluid connection 1022) or as a separate chamber with a fluid connection to the indentation. The channel may extend only around a part (i.e. not all of the way around) the indentation, such that the channel may be generally semi-circular in shape.

A plurality of fluid connections 1022 may alternatively be included in the dressing. Rather than being recessed into the first side 1012, the fluid connection(s) may be internal to the patch. In an alternative, waste may be stored within the indentation itself. In such embodiments, a large indentation may be provided, and consequently the dressing may be of a larger size than in previously described embodiments.

The user may remove and replace the bag in other alternative ways, for example by (reversibly) dissembling the patch at a mid-point, or by uncovering an aperture for accessing the bag in the second side 1014. The bag may alternatively be formed as an inner liner of the channel 1020.

It will be appreciated that the dressing described may not only be used by ostomates, but also by any other users having structures, which may be undesirable or unsightly, extending above their skin as a result of a previous wound or surgical procedure. Examples of such other structures include scars or deformities, which may be incorporated into suitably sized indentations 16 to be concealed. A channel or other further indentation may be provided to allow waste (such as discharges of blood or pus) to be received from these structures.

The dressing may also be used without an indentation 16 or any deodorising material (for example, the membrane 417*c*) when used for scarring or deformities on the surface of the skin. As such, in this case the first side of the patch is simply a flat adhesive face which can adhere straight on to the body. In this embodiment, adhesive may only be provided on certain areas of the first side, so as to avoid any risk of irritation of the area to be concealed.

Optionally, the vent may be provided as an integral part of the patch, for example, the vent may surround a raised element. The vent may comprise an odour absorbent membrane and a plurality of outlets provided in the patch and film.

As briefly mentioned, the patch and/or a mould for the patch of one or more embodiments described herein may optionally be manufactured by way of '3D printing' whereby a three-dimensional model is supplied, in machine-readable form, to a '3D printer' adapted to manufacture said patch and/or mould. This may be by additive means such as extrusion deposition, Electron Beam Freeform Fabrication (EBF), granular materials binding, lamination, photopolymerization, or stereolithography or a combination thereof. The machine-readable model comprises a spatial map of the object or pattern to be printed, typically in the form of a Cartesian coordinate system defining the object's or pattern's surfaces. This spatial map may comprise a computer file which may be provided in any one of a number of file conventions. One example of a file convention is a STL (Stereo Lithography) file which may be in the form of ASCII (American Standard Code for Information Interchange) or binary. STL files specify areas by way of triangulated surfaces with defined normals and vertices.

An alternative file format is AMF (Additive Manufacturing File) which provides the facility to specify the material and texture of each surface of the patch and/or mould as well as allowing for curved triangulated surfaces. The mapping of the patch and/or mould may then be converted into instructions to be executed by 3D printer according to the printing method being used. This may comprise splitting the model into slices (for example, each slice corresponding to an x-y plane, with successive layers building the z dimension) and encoding each slice into a series of instructions. The instructions sent to the 3D printer may comprise Numerical Control (NC) or Computer NC (CNC) instructions, preferably in the form of G-code (also called RS-274), which comprises a series of instructions regarding how the 3D printer should act. The instructions vary depending on the type of 3D printer being used, but in the example of a moving printhead the instructions include: how the printhead should move, when/where to deposit material, the type of material to be deposited, and the flow rate of the deposited material.

Any part of the dressing, patch, and/or mould described herein may be embodied in one such machine-readable model, for example a machine-readable map or instructions, for example to enable a physical representation of said part of the dressing to be produced by 3D printing. This may be in the form of a software code mapping of one or more components and/or instructions to be supplied to a 3D printer (for example numerical code).

It will be understood that the present invention has been described above purely by way of example, and modifications of detail can be made within the scope of the invention.

What is claimed is:

1. A dressing for concealing a stoma on a human body, the dressing comprising:
    a patch arranged to be placed on the body over the stoma to conceal the stoma, wherein the patch comprises:
        a concave first side and a concave second side arranged to face away from the first side; the first side comprising: a first side opening centrally located on the first side; and an outer ring around the first side opening and arranged to be placed against the body around the stoma;
        a chamber extending distally from the first side opening and within the concave first side; the chamber configured to hold at least a portion of a disposable bag for receiving waste from the stoma;
        a central indentation within or adjacent to the first side opening and the chamber, the central indentation for receiving the stoma;
        one or more apertures disposed between the first side and the second side distal to the indentation and configured to allow gases to be vented out of the chamber via the second side;
        a generally annular ring comprising an anti-bacterial component, the annular ring at least partially fitting within a first channel within or adjacent to the central indentation and around the first side opening of the patch;
    wherein the anti-bacterial annular ring is configured to fit around the stoma such that an inner surface of the annular ring is in direct contact with the stoma; and wherein the annular seals the patch around the stoma;
        an adhesive provided on at least the proximal surfaces of: the outer ring and the anti-bacterial annular ring to adhere the patch to skin around the stoma; and;
        a second channel around the first channel and configured to hold and seal the opening of the disposable bag such that waste from the stoma enters the bag while also allowing the gases to be vented out of the chamber through the one or more apertures;
    the disposable bag configured for receiving waste from the stoma, wherein the disposable bag is held within the chamber in the patch so as to conceal the disposable bag when the patch is placed on the body and when the disposable bag is in use in receiving waste from the stoma.

2. A dressing according to claim 1, further comprising an odour resistant absorbent membrane disposed in the central indentation and arranged such that gases are vented through the one or more apertures via the membrane.

3. A dressing according to claim 1, further comprising means for sealing the one or more apertures so as to inhibit gases from being vented from the central indentation.

4. A dressing according to claim 1, wherein the chamber is a further indentation in the patch.

5. A dressing according to claim 1, wherein the first channel is a generally annular channel arranged to encircle the central indentation.

6. A dressing according to claim 1, wherein the chamber is provided in fluid communication with the central indentation.

7. A dressing according to claim 1, wherein the patch further comprises a three-dimensional formation covering at least the one or more apertures and arranged to face away from the body.

8. A dressing according to claim 7, wherein the formation is arranged to coincide with the position of a protrusion in the second side of the patch formed distal to the chamber, such that the protrusion is disguised by the formation when viewed from the second side of the patch.

9. A dressing according to claim 1,
    wherein a three dimensional (3D) formation is provided on at least part of the second side of the patch, said three dimensional formation being arranged to face away from the body when the patch is placed on the body so as to conceal the stoma.

10. A dressing according to claim 9, wherein the formation is arranged as a decorative formation and wherein the formation has an irregular shape.

11. A dressing according to claim 1, wherein wherein the adhesive is a bio-grade adhesive.

12. A method of manufacturing a dressing according to claim 1, comprising:
    obtaining one or more dimensions of the stoma to be concealed by the patch;
    forming the patch arranged to cover an area greater than the area covered by the stoma on the body;
    providing the central indentation in the patch according to claim 1;
    wherein the central indentation is configured to receive the stoma when the patch is placed on the body, whereby to conceal the stoma.

* * * * *